US00PP23757P3

(12) United States Plant Patent
Higaki

(10) Patent No.: US PP23,757 P3
(45) Date of Patent: Jul. 23, 2013

(54) ***HYDRANGEA* PLANT NAMED 'BC6.1'**

(50) Latin Name: ***Hydrangea macrophylla* (Thunb.)**
Varietal Denomination: BC6.1

(75) Inventor: Harrison M. Higaki, San Mateo, CA (US)

(73) Assignee: Bay City Flower Company, Inc., Half Moon Bay, CA (US)

( * ) Notice: Subject to any disclaimer, the term of this patent is extended or adjusted under 35 U.S.C. 154(b) by 80 days.

(21) Appl. No.: 13/135,028

(22) Filed: Jun. 22, 2011

(65) Prior Publication Data

US 2012/0331600 P1 Dec. 27, 2012

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — June Hwu
(74) *Attorney, Agent, or Firm* — James R. Cypher; Charles R. Cypher

(57) ABSTRACT

A new and distinct cultivar of *Hydrangea macrophylla* (Thunb.) named 'BC6.1' originated as a controlled cross between unpatented varieties. The cultivar 'BC6.1' can be blue or red depending on the acidity of the soil and the presence of aluminum. The variety 'BC6.1' has large attractive inflorescences with large sepalous florets, distinct sepal pigmentation and good commercial characteristics. When grown in the presence of aluminum, the under side of the sepals is R.H.S. 86 A (violet group), the underside of the sepals is R.H.S. 88 D (violet group).

4 Drawing Sheets

Botanical classification: *Hydrangea macrophylla* (Thunb.) 'BC6.1'.

Variety denomination: 'BC6.1'.

BACKGROUND OF THE INVENTION

This invention relates to a new and distinct cultivar of the Saxifragaceae family. The botanical name of the plant is *Hydrangea macrophylla* (Thunb.) 'BC6.1'.

The new cultivar originated as a seedling from a controlled cross between the unpatented variety known as 'LK49' which was the seed parent and the unpatented, commercial variety 'Amsterdam' which was the pollen parent. 'LK49' is relatively compact plant with wiry stems, relatively small leaves, relatively small sepalous florets, and inflorescences that are resistant to being damaged by conditions in commercial coolers. 'Amsterdam' is a relatively compact plant with relatively thick stems, relatively large leaves, and medium sized sepalous florets. The inflorescences of 'Amsterdam' are not particularly resistant to being damaged by conditions in commercial coolers.

The variety 'BC6.1' has large attractive inflorescences with relatively large sepalous florets, attractive sepal pigmentation and good commercial characteristics. The variety 'BC6.1' has pigmented sepals, and was grown under pH conditions that produce blue pigmentation. The color of the sepals changes as the plant ages. Below is a table comparing the new variety to similar varieties. The variety 'Grace', which is the subject of U.S. Plant patent application Ser. No. 12/930,413 was developed during the same cross as 'BC6.1' and has the same seed parent and same pollen parent.

TABLE 1

| | New Variety 'BC6.1' | patent application Pending Ser. No. 12/930,413 'Grace' | U.S. Plant Pat. No. 18,593 'True Blue' | U.S. Plant Pat. No. 22,575 'Galilee' |
|---|---|---|---|---|
| Leaf size | 12 cm wide × 15 cm long | 13 cm wide × 16 cm long | Unknown | 13.5 cm wide × 21 cm long |
| Stem strength | Stems are strong but benefit from being staked | Stems are strong but benefit from being staked | Strong | Strong |
| Sepal Pigmentation | Upperside of sepals is R.H.S. 86 A (violet group); Underside of sepals is R.H.S. 88 D (violet group) | Upperside of sepals is R.H.S. 63 A (red-purple group); Underside of sepals is R.H.S. 63 D (red-purple group) | Both sides of sepalsa are R.H.S. 100 D (blue group). | R.H.S. 100 B (blue group). Produces blue pigmentation with relatively little alumina |
| Sepal Floret Size | 60 mm to 70 mm | 70 mm to 100 mm | 50 mm to 60 mm | 60 mm |

The new cultivar 'BC6.1' has been successfully asexually reproduced under controlled environmental conditions at a nursery in Half Moon Bay, Calif. under the direction of the inventor with its distinguishing characteristics remaining stable.

Asexual reproduction was first accomplished when vegetative cuttings were taken from the initially selected plant. Examination of asexually reproduced, successive generations grown in Half Moon Bay, Calif. show that the combination of characteristics as herein disclosed for 'BC6.1' remains firmly fixed through three generations.

DESCRIPTION OF THE DRAWINGS

The accompanying drawings consist of color photographs that show the typical plant form, including the inflorescence, foliage, and sepals.

DESCRIPTION OF THE NEW PLANT

Figure 1:
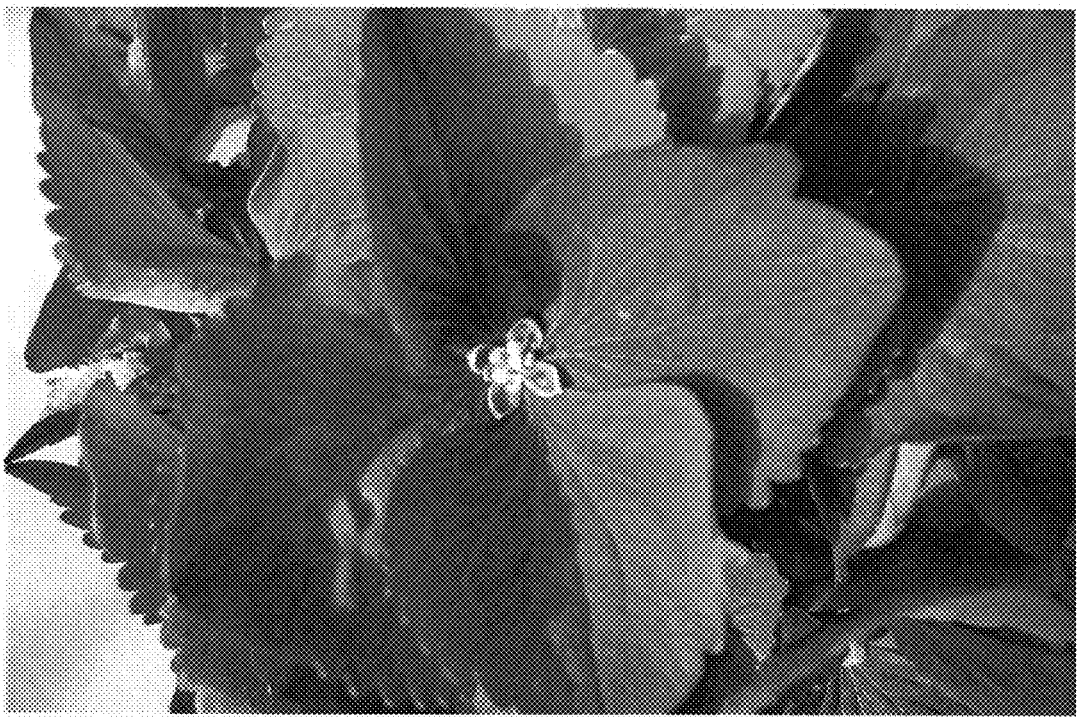
FIG. 1 is a close-up view of a sepalous floret of the new variety.
Figure 2:
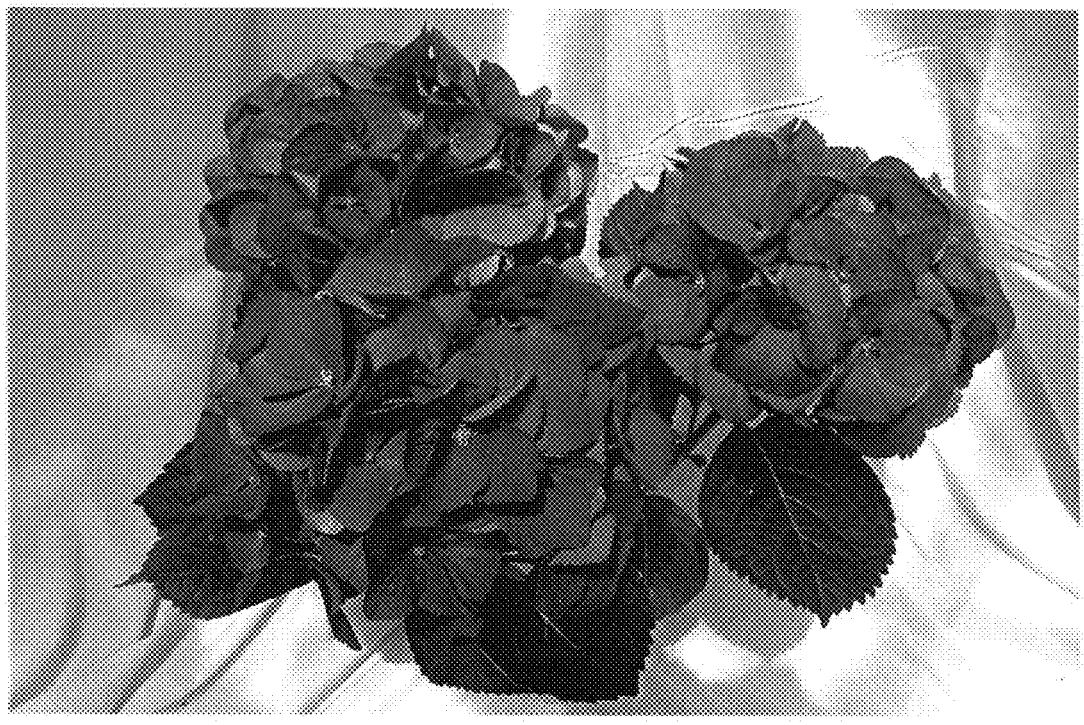
FIG. 2 is a view of the entire plant showing its form, growth habit, dark green foliage, inflorescence, and the color of its sepals.
Figure 3:
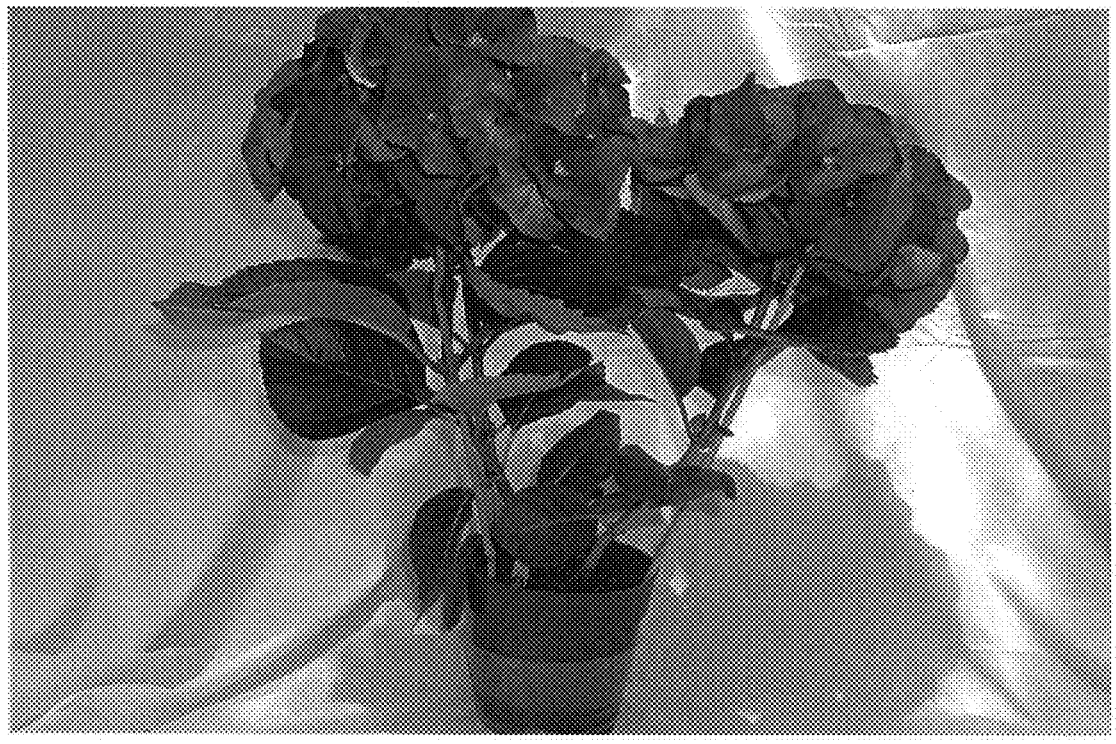
FIG. 3 is a view of the entire plant showing its form, growth habit, dark green foliage, inflorescence, and the color of its sepals.
Figure 4:
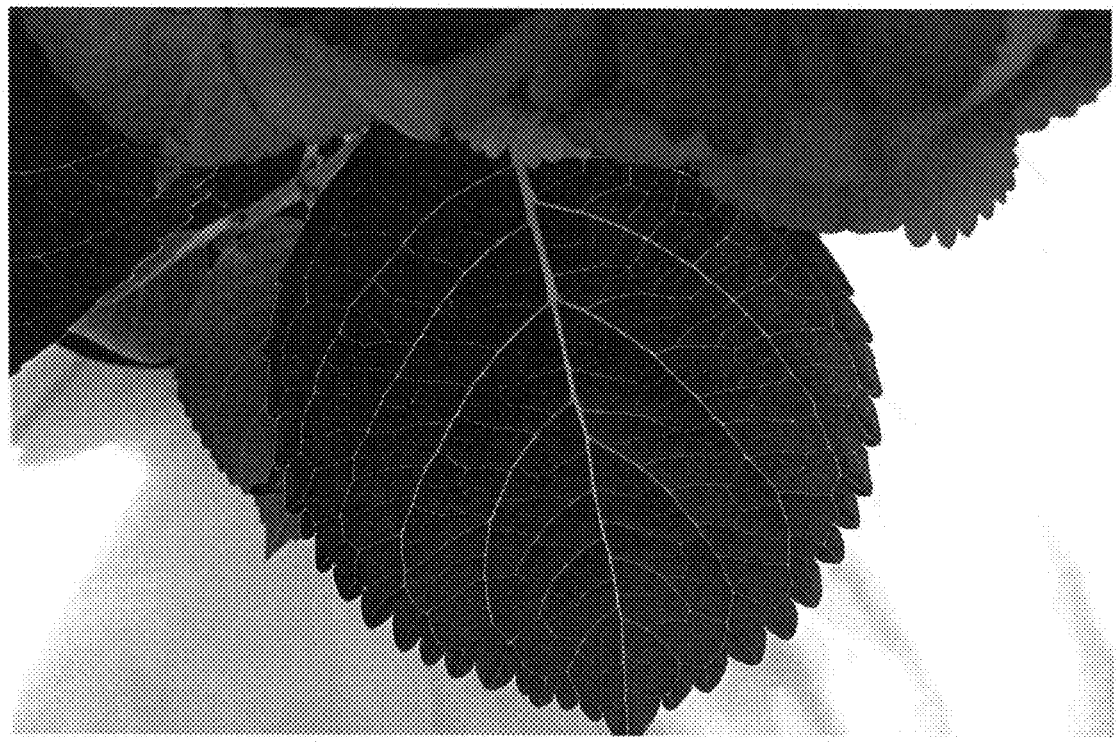
FIG. 4 is a close-up view of the adaxial surface of a mature leaf.
Figure 5:
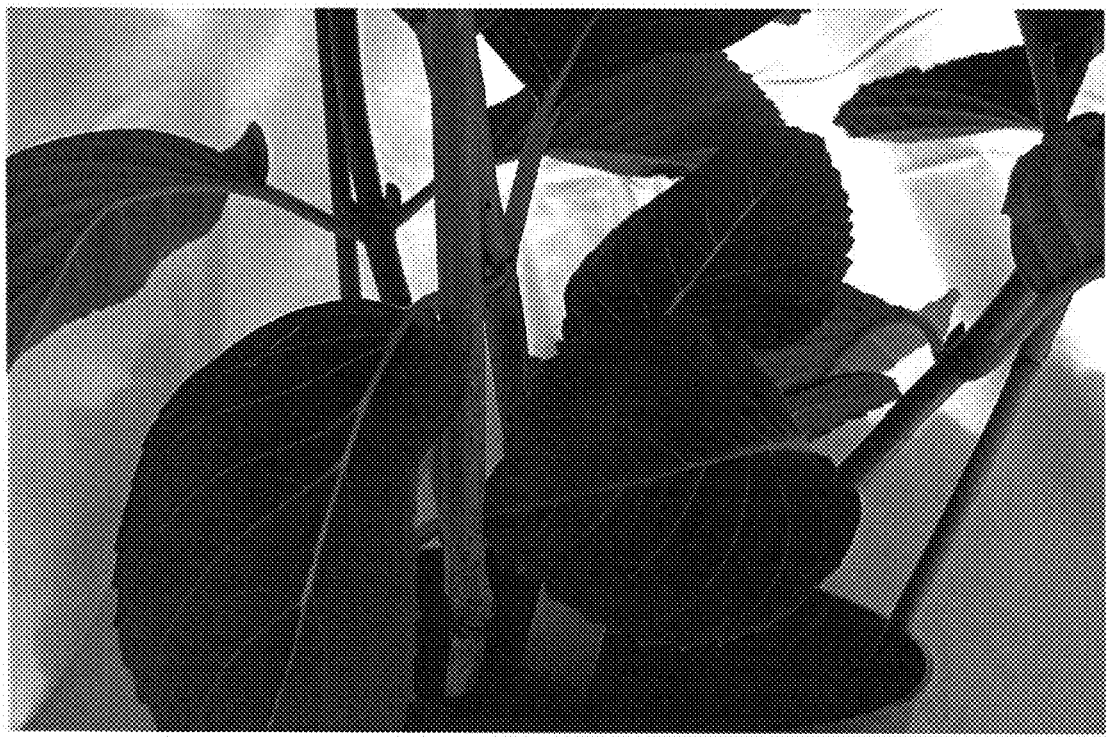
FIG. 5 is a close-up view of the base of the stem.
Figure 6:
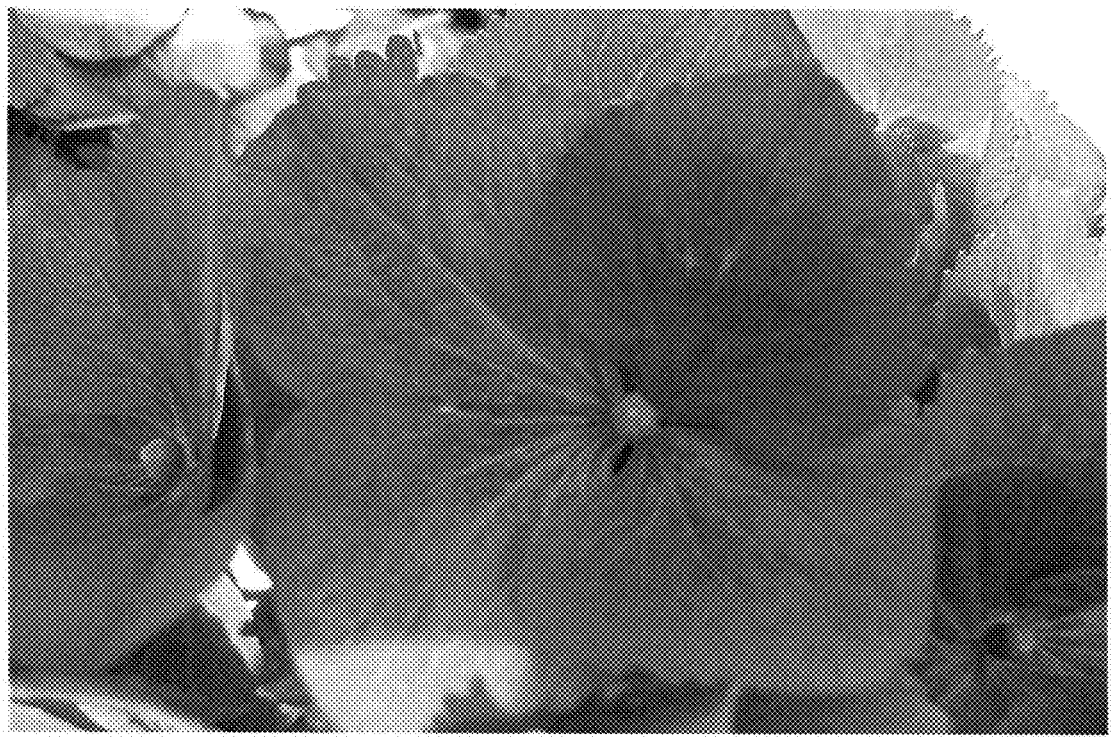
FIG. 6 is a close-up view of a sepalous floret of the new variety.
Figure 7:
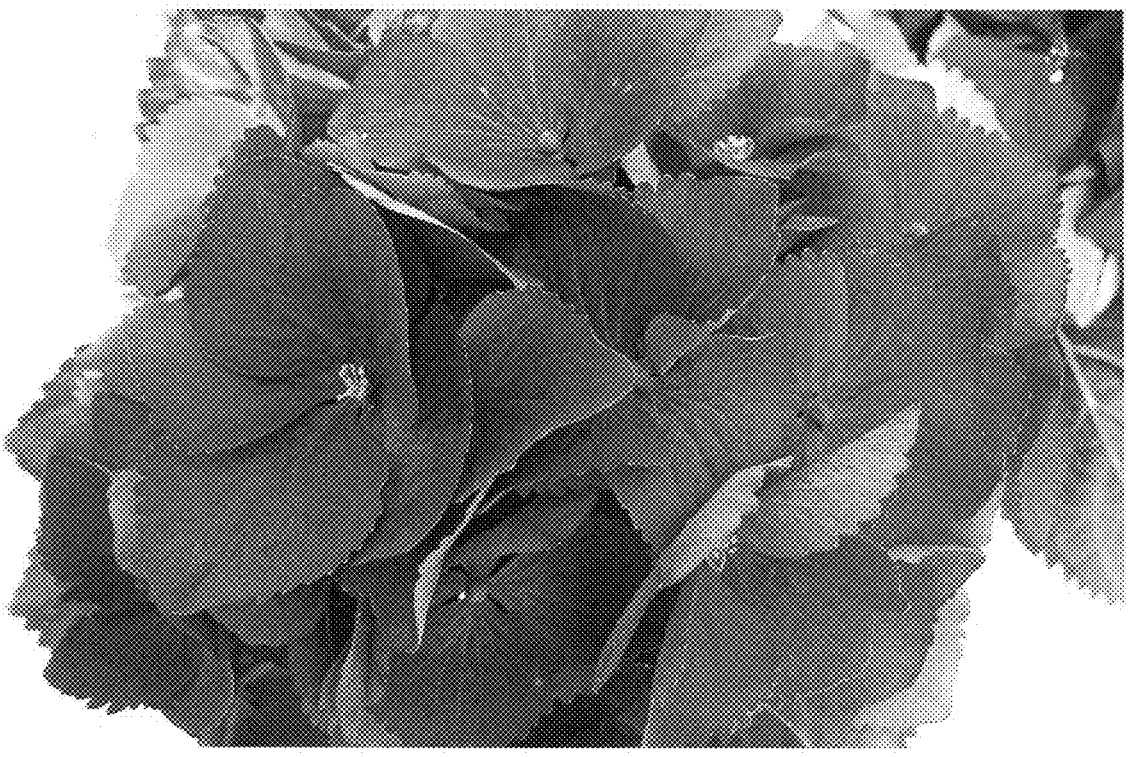
FIG. 7 is a close-up view of the upperside of a panicle of the new variety.
Figure 8:
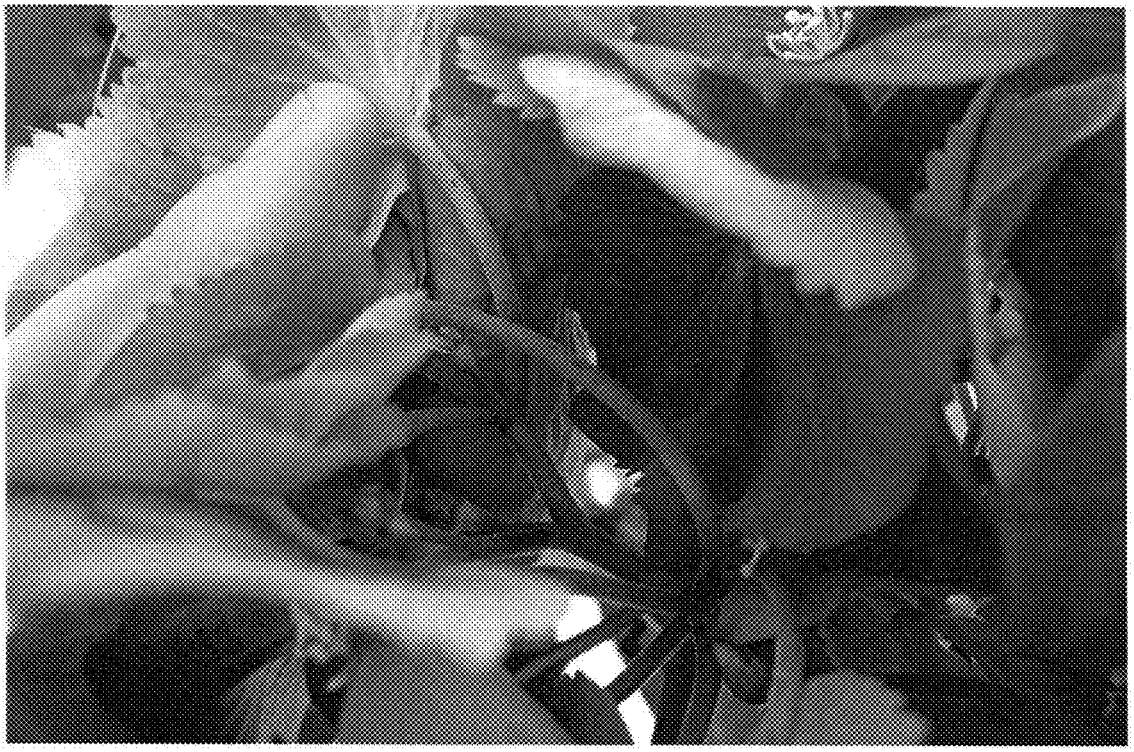
FIG. 8 is a close-up view of the center of a panicle of the new variety, showing sepalous florets and non-sepalous florets.

The plants shown in the figures are approximately 50 weeks old. The plant started out as cuttings, taken from the stem of a grown plant. The cuttings were placed in a pot and the soil was periodically treated with aluminum to produce blue pigmentation. The plant was pinched early to promote lateral branches.

'BC6.1' has not been observed under all possible environmental conditions. The phenotype may vary significantly with variations in environment such as temperature, light intensity and day length. Color determinations were made with The Royal Horticultural Society (R.H.S.) Colour Chart, in association with the Flower Council of Holland, located in Lieden.

THE PLANT

Origin: Controlled cross. The new cultivar originated as a seedling from a controlled cross between the unpatented variety known as 'LK49' which was the seed parent and the unpatented, commercial variety 'Amsterdam' which was the pollen parent.

Form: Upright, compact shrub. A typical plant with a mature inflorescence that is ready for sale is approximately 15" high (with stakes) and has a diameter of 18" when grown in a 6" pot with appropriate soil amendments. The pictured plant had three stems with one inflorescence per stem with 1 cutting per pot.

Growth: Upright, vigorous growth habit. Inflorescence is large. The plant branches easily with shoots forming at the base of the plant. Lateral branches are similar in appearance and form to the main stems.

Stems: Lenticels are present. Lenticels are R.H.S. 86 A (violet group) and are 1 to 2 mm long. The surface of young stems is glabrous. Stems become woody as they age. The color of typical young stems and young lateral branches is R.H.S. 144 A (green group). The older portions of the stems are R.H.S. 199 B (grey-brown group) Younger portions of the stems are 7 to 9 mm in diameter. Older portions of the stems are 7 to 9 mm in diameter.

Foliage: Abundant. Leaves are opposite on stem and lateral branches.

*Shape of leaf.*—Elliptic with acute base and apex. Margins are serrate.

*Texture.*—Glabrous; veins dominate on the underside of the leaf and are sunken on the upper leaf surface.

*Color.*—Mature leaves have an upper side that is R.H.S. 147 A (yellow-green group), and an under side that is R.H.S. 138 B (green group). Leaves are pinnately veined. The midvein and veins branching off the midvein are large and prominent on the underside of the leaves. Veins are R.H.S. 138 B (green group). Leaves are as wide as 12 cm and 15 cm long. Petioles are smooth and 2.5-3.5 cm long and 4 mm wide. Petioles are R.H.S. 138 B (green group).

BUDS

Form: Globose with 4 to 5 connate, elliptic, smooth petals. Most buds have 4 petals, whether they will mature into sepalous or non-sepalous florets. Buds in the center of the inflorescence are non-sepalous. The majority of buds will develop into sepalous florets. They are approximately 1 mm by 1 mm when very young. Buds can be 4 mm in diameter and still be unopened.

Aspect: Smooth.

Arrangement: Borne on branched panicles.

INFLORESCENCE

Form: Paniculate. Terminal. As many as 100 individual flowers (florets) per inflorescence. Both sepalous florets and non-sepalous florets borne on same panicle. Flowers do not produce a fragrance. The peduncle for the inflorescence is strong and upright. Very few non-sepalous florets developing early on cymes that are later hidden by sepalous florets. Florets, both sepalous and non-sepalous, have anthers and style. Inflorescences are long-lasting, up to six weeks.

Size of inflorescence: Large and globose. Individual inflorescence size is dependent on the number of florets. A typical inflorescence can grow as large as 8" in diameter, and be 4" high.

Shape: Clusters of numerous small florets; sepalous florets overlap one another. Sepals are persistent.

Appearance: Showy.

FLORETS

General: The non-sepalous florets at the center of the inflorescence open first. Sepalous and non-sepalous florets are perfect and complete.

*Corolla.*—Generally, for both sepalous and non-sepalous florets there are 4 petals which fall off as flower matures. Petals are typically 4 mm long and 3 mm wide. Pedicel length for non-sepalous florets averages 4 mm. Pedicel length of sepalous florets is between 30 and 40 mm in length for plants of this age. Pedicels of both sepalous and non-sepalous florets continue to elongate as the inflorescence ages. Lenticels are present on pedicels, lenticels are no more than 1 mm long. Lenticels of both sepalous and non-sepalous florets are primarily R.H.S. 59 B (red-purple group) and R.H.S. 64 B (red-purple group). Pedicel of both sepalous and non-sepalous florets are primarily 96 C (violet-blue group) and 83 A (violet group).

Stamens: 8 stamens. Pollen is R.H.S. 155 C (white group). Plant produces abundant pollen. Filament is approximately 2 to 3 mm long. Filament is R.H.S. 155 C (white group). Anther is 1 mm long and is regular and basally attached.

Stigma: Two to three style each, although most florets have two style. Each style has one stigma. Style is typically 2 mm long. Style is R.H.S. 151 C (yellow-green group). Stigma is R.H.S. 92 A (violet-blue group).

Ovary: Ovary is partially inferior.

Sepalous florets:

*General.*—Veins dominate on the underside of the sepals.

*Number of sepals.*—4 or 5 sepals per floret, usually 4.

*Aspect of sepals.*—Smooth and glaucescent.

*Shape of sepals.*—Reniform with acuminate apex. Edges are entire, but with some crenation.

*Size of sepals.*—As the florets mature, the sepals enlarge and overlap each other more and more, until, often, there is no space between the sepals when the petals of the florets open. Sepals at maturity are typically 4.0 cm long and 4.0 cm wide. Flowers are typically 6 to 7 cm in diameter. The uppersides of the sepals are R.H.S. 86 A (violet group) and the undersides are R.H.S. 88 D (violet group). Blue pigmentation develops at the tips of the sepals and travels inward towards base of the sepals.

Fruit: None.

Disease and pest resistance: Unknown.

I claim:

1. A new and distinct *Hydrangea macrophylla* plant named 'BC6.1' substantially as herein shown and described.

* * * * *